United States Patent [19]
Pettine et al.

[11] Patent Number: 5,242,448
[45] Date of Patent: Sep. 7, 1993

[54] BONE PROBE

[76] Inventors: Kenneth A. Pettine, 1130 Oakleaf Ct., Ft. Collins, Colo. 80525; James D. Stice, 1907 Sharon Ave., Minneapolis, Minn. 55414; Timothy J. Ley, 5251 Morgan Ave. N., Minneapolis, Minn. 55430

[21] Appl. No.: 739,248

[22] Filed: Aug. 1, 1991

[51] Int. Cl.⁵ .................................................. A61B 5/10
[52] U.S. Cl. ....................................... 606/102; 606/78
[58] Field of Search ..................................... 606/78, 102

[56] References Cited

U.S. PATENT DOCUMENTS

| | | | |
|---|---|---|---|
| 3,738,355 | 6/1973 | Salvatore | 606/102 |
| 4,616,656 | 10/1986 | Nicholson et al. | 128/630 |
| 5,010,892 | 4/1991 | Colvin et al. | 128/774 |
| 5,013,318 | 5/1991 | Spranza, III | 606/102 |
| 5,067,957 | 11/1991 | Jervis | 606/78 X |

Primary Examiner—Mickey Yu
Attorney, Agent, or Firm—Richard E. Brink

[57] ABSTRACT

An orthopedic bone probing device to locate cavities, holes, and crevices in bones. For instance, where holes are drilled in bones to accommodate fastening devices it is important to ascertain if there are any sites where the drilling penetrated the entire side wall of the bone resulting in an undesirable hole in the side wall of the bone. The device of this invention consists of a cannula containing a shaft of superelastic material that assumes a retractable position angular to the axis of the cannula upon being ejected from one end of the cannula and the other end of the cannula is retained by a plunger that limits the amount of shaft that can be ejected and necessitates the removal of the shaft if the cannula is to be removed.

6 Claims, 2 Drawing Sheets 5,242,448

BONE PROBE

BACKGROUND AND SUMMARY OF THE INVENTION

The invention relates to an orthopedic bone probing device which makes it possible for the surgeon to insert the device into any small opening in the bone which he intends to use in his operation and to ascertain if there are any holes or void areas in the side walls of the bone. This device is comprised of a cannula into which is inserted a shaft of superelastic material which bends upon being ejected out one end of the cannula and is attached at the other end to a plunger for pushing the shaft out of the cannula to the degree that the length of the shaft is greater than the length of the cannula.

This probing device is especially useful in spine surgery where the physician has drilled a hole into which he will insert a fastener. It is highly desirable for the surgeon to confirm that he has not opened up a hole in the side wall of the bone structure. The bone probes used prior to this invention were rigid rods which have a curve or hook at the end. With these rigid devices, the surgeon had difficulty inserting the hooked rod through a small diameter opening in the bone to ascertain the integrity of the bone or depth of any hole. In other words, the diameter of the rod and fixed hook were greater than the diameter of most bone holes. If the diameter of the fixed hook was reduced, it was no longer useful for probing the side walls of the bone structure. The value of the retractable probe is its ability to be inserted into small openings in the bone and then be extended out to serve as a useful bone probe.

An objective of this invention is to provide an orthopedic probe which can locate cavities (imperfections or void areas) of the bone structure to be used by the surgeon.

Another objective of the invention is to provide a probe in which the surgeon can measure the depth of any imperfection.

Another objective of the invention is to provide a device for measuring the diameter of bone structures.

A still further objective to provide a probe where the tip of the probe can be observed by imaging, such as by x-ray.

DRAWINGS

Figure 10:
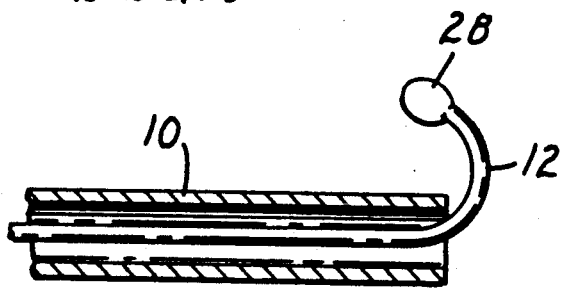

FIG. 10 is a cross-sectional side view of the end of the cannula 10 in which the extended shaft 12 terminates in a loop 28 which may be used when suturing is desired.

Figure 11:
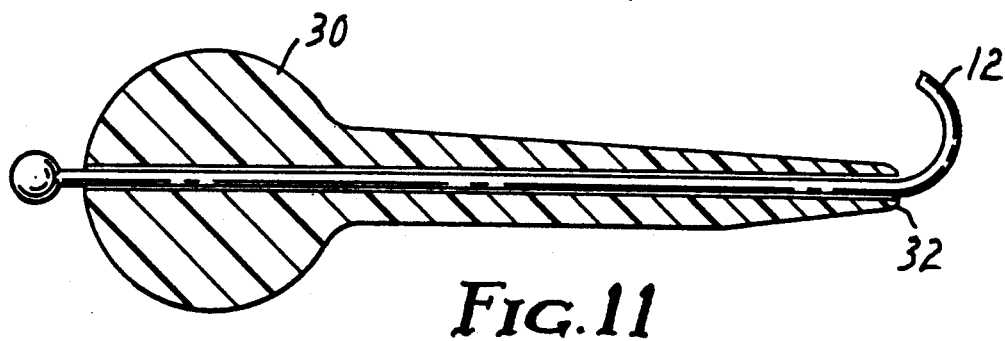

FIG. 11 is a side view of the bone puncturing device 30, commonly known as a "gear shift", because of its shape which has a blunt piercing end and hollow structure to accommodate the shaft 12 which can be ejected from the blunt tip 32.

Figure 12:
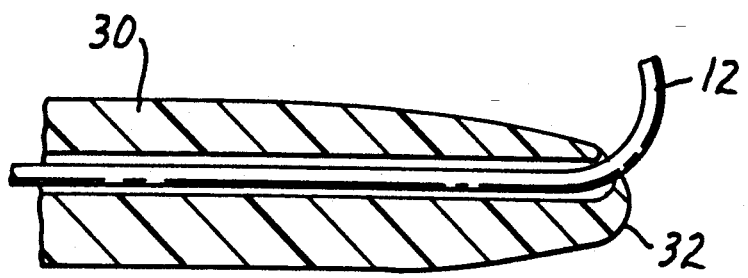

FIG. 12 is a cross-sectional side view of the end of the puncturing device 30 in which the shaft 12 can be ejected off center and on the side of the blunt tip 32.

DESCRIPTION OF THE PREFERRED EMBODIMENTS

The cannula 10 and the shaft 12 are combined by inserting the shaft 12 into the interior of the cannula 10. (FIGS. 1-11). Generally speaking, the cannula 10 will be 3 to 36 inches long.

Figure 1:
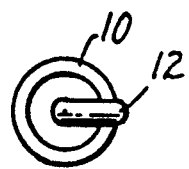
FIG. 1 is a top view of the cannula with the shaft inside and not extended.
Figure 2:
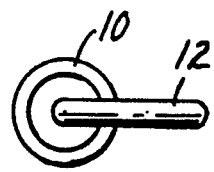
FIG. 2 is a top view of the cannula with the shaft extended and curved.
Figure 3:
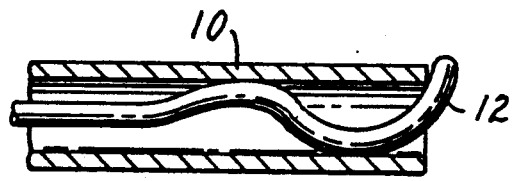
FIG. 3 is a cross-sectional side view of this invention in which the shaft is not extended.
Figure 4:
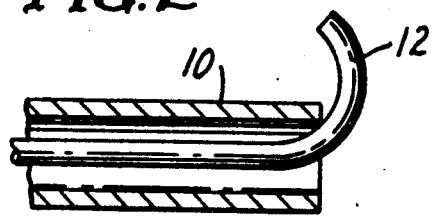
FIG. 4 is a cross-sectional side view of this invention in which the shaft is extended at a right angle to the axis of the cannula and beyond the side of the cannula as it would be when a void space is present.
Figure 5:
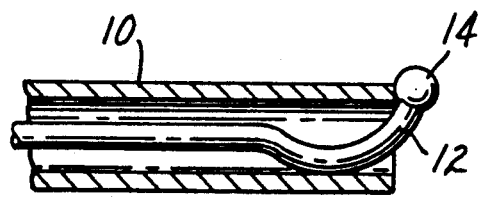
FIG. 5 is a cross-sectional side view of this invention in which the shaft is flush with the side of the cannula as it would be when the side wall is solid.
Figure 6:
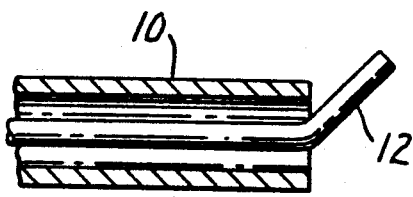
FIG. 6 is a cross-sectional side view of this invention in which the shaft is extended at an angle of 45° to the axis of the cannula.

The blunt tip of the shaft 12 in FIG. 5 has been enlarged to provide a ball-like tip 14 where this feature will further minimize damage to tissue in the vicinity of the bone.

Figure 7:
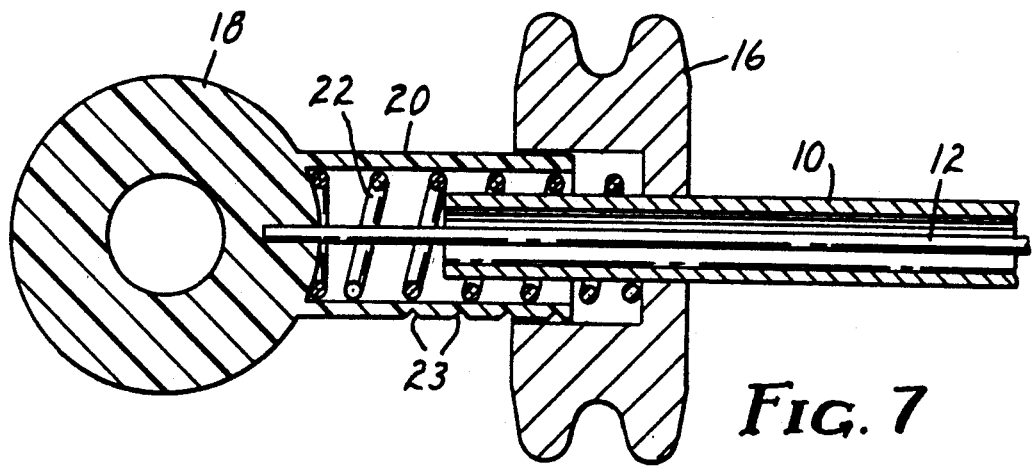
FIG. 7 is a cross-sectional side view of the bone probe having a spring retaining mechanism.

The side view, FIG. 7, illustrates the bone probe of this invention in which the cannula 10 is embedded in the retainer 16 and the shaft 12 is embedded in the plunger 18 attached to a cannula 20 of larger diameter than cannula 10. Cannula 20 can also be calibrated 23 for measurement features. A spring 22 is retained between the movable retainer 16 and the plunger 18 to provide a spring-loaded mechanism to pull the shaft 12 under tension into the cannula 10.

Figure 8:
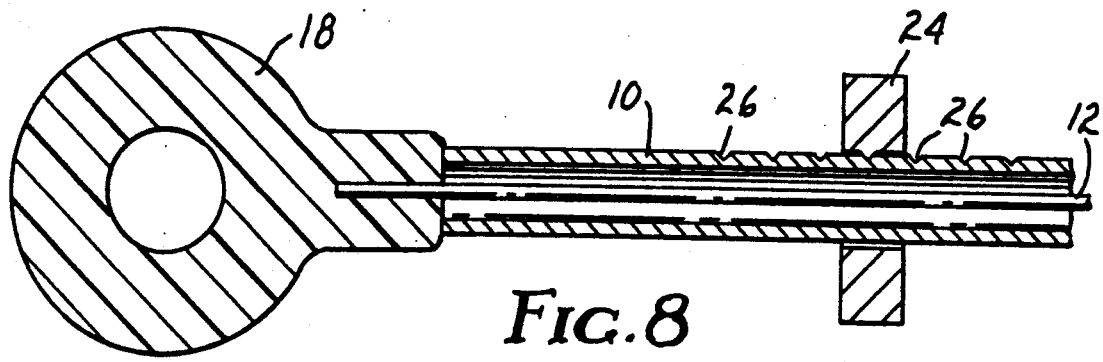
FIG. 8 is a cross-sectional side view of the bone probe.
Figure 9:
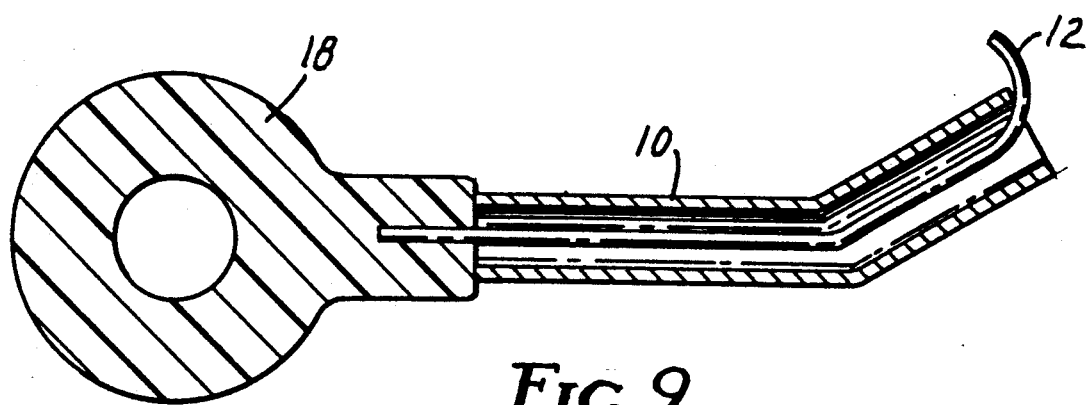
FIG. 9 is a cross-sectional side view showing the cannula 10 and shaft 12 as a curve format for accessing bone structures in this and related angular configurations.

The side view, FIG. 8, illustrates the bone probe of this invention in which a slideable stopper 24 is attached to cannula 10 which has been calibrated 26 to give a direct reading of the distance from the tip of the "J" shaft 12.

The preferred shafts of this invention are prepared from 0.034 inch diameter nitinol wire. This diameter may vary from 0.025 to 0.050 inches. One end of the wire is bent over a forming tool such that the blunt tip is in a "J" shape (see FIG. 4) and approximates a 90° bend in the shaft. The "J" shaped shafts are then heated to about 500° C. for a period of 5-30 minutes, removed from the forming tool, polished and ready to use.

The superelasticity of the nitinol metal "J" shafts in such that they may be straightened for insertion in a cannula having an inside diameter of 0.072 inch and an outside diameter of 0.095 inch. When the pre-conditioned "J" shaped shaft is extended beyond the tip of the cannula, which is rounded, smooth and coated if necessary to provide a low friction area in contact with the shaft, it returns to the "J" shape. It is preferable that the inside diameter of the cannula be approximately twice the width of the shaft and that the outside diameter of the cannula be as small as possible. For shipping, handling and storage, it is best for the shaft to be in the "J" form.

When used by the orthopedic surgeon inside a cavity in a bone structure, it is used to probe the side walls of the cavity. If the blunt tip extrudes no further than the side wall of the cannula, the cavity which is normally a hole drilled by the surgeon, is in its preferred form. If the probe extends beyond the side wall of the cannula, a secondary cavity, or hole in the side wall, has been located. When a secondary cavity is observed, the surgeon may take whatever remedial action is required or drill a second hole which hopefully, will not have any secondary cavity.

In the case of spine surgery, the immediate vicinity of bone structure is surrounded by very sensitive tissue and nerves. The probe of this invention is much less disruptive of tissue and nerves than existing rigid probes.

1. Revision hip surgery to probe sides of femur to look for cracks and holes in the femur;
2. When placing hip screws in the femoral head to see if the tapped hole has broken through;
3. For slipped capital femoral epiphysis;
4. Probing a fractured femoral neck;
5. Probing the space between the malleoli and the talus in ankle fractures; and
6. The bone probe can create holes in bone by pushing through bone while having inner shaft extend and retract to be certain bone probe hasn't penetrated outside bone.

The bone probe can also be used as a measuring device by hooking the "J" at one end of the bone to be measured. For instance, the probe could be inserted through a hole in a bone and the width of the bone measured in this manner. This measurement is then used to determine the length of screw needed. One method of measurement is illustrated in FIG. 8 where a movable marker may be positioned at one end and the "J" shaft end is at the other end. The cannula can be calibrated so as to give a direct reading of the width of the bone measured.

A number of shape-memory alloys (SMA) are known to exhibit the superelastic/pseudoelastic shape recovery characteristic for use in this invention. Such alloys generally are characterized by their ability, at room/body temperature, to be deformed from an austenitic crystal structure to a stress-induced martensitic structure, returning to the austenitic state when the stress is removed. The reverse shape transformation gives the alloy superelastic or pseudoelastic properties. Alternatively, a cold worked martensitic microstructure can be used to give enhanced shape recovery over other metallic materials. Nitinol, an alloy of nickel and titanium, is a particularly preferred alloy in that it is commercially available and has been studied somewhat more than many other SMA's.

We claim as our invention:

1. An orthopedic bone probing device comprising a cannula for insertion into a passageway of a bone structure and a super-elastic shaft having a blunt tip and being movable within the lumen of the cannula, said shaft upon ejection from the end of the cannula assuming an angular projection from the axis of the cannula, said shaft being an integral part of a plunger that facilitates ejection of the blunt tip on the shaft and retains the cannula in position such that it cannot be removed from the patient while the probe is inside the bone structure.

2. The device of claim 1 in which the shaft is a shape memory alloy.

3. The device of claim 1 in which the shaft is nitinol.

4. The device of claim 1 in which the angular projection approximates 90°.

5. The device of claim 1 in which the cannula is calibrated to measure the width of the bone.

6. An orthopedic bone probing device comprising a cannula for insertion into a passageway of a bone structure and, slidably positioned within said cannula, a single super-elastic shaft having a blunt tip, said shaft upon ejection from the end of the cannula assuming an angular projection from the axis of the cannula, said shaft being an integral part of a plunger that facilitates ejection of the blunt tip on the shaft and retains the cannula in position such that it cannot be removed while the probe is inside the bone structure.

* * * * *